(12) United States Patent
Hiramoto et al.

(10) Patent No.: US 7,098,244 B2
(45) Date of Patent: Aug. 29, 2006

(54) ANTIBACTERIAL AGENT

(75) Inventors: Tadahiro Hiramoto, Hiratsuka (JP); Ryo Takeuchi, Hiratsuka (JP); Minoru Hanada, Hiratsuka (JP); Fumitaka Norose, deceased, late of Odawara (JP); by Ritsuko Norose, legal representative, Odawara (JP)

(73) Assignee: Takasago International Corporation, Tokyo (JP)

( * ) Notice: Subject to any disclaimer, the term of this patent is extended or adjusted under 35 U.S.C. 154(b) by 406 days.

(21) Appl. No.: 10/100,189

(22) Filed: Mar. 19, 2002

(65) Prior Publication Data

US 2003/0068389 A1 Apr. 10, 2003

(30) Foreign Application Priority Data

Mar. 19, 2001 (JP) ............................. 2001-079489

(51) Int. Cl.
*A01K 43/16* (2006.01)
*A61K 35/78* (2006.01)

(52) U.S. Cl. ...................... 514/457; 424/725; 424/736; 424/777

(58) Field of Classification Search ................ 424/726, 424/58, 736, 725, 777; 514/27, 457
See application file for complete search history.

(56) References Cited

U.S. PATENT DOCUMENTS

| 4,925,660 A | 5/1990 | Atsuta et al. | 424/81 |
| 5,457,030 A | 10/1995 | Badal et al. | 435/34 |
| 5,985,912 A | 11/1999 | Yang et al. | 514/422 |

FOREIGN PATENT DOCUMENTS

| EP | 0 515 217 A1 | 11/1992 |
| GB | 986287 A | 3/1965 |
| GB | 1110848 A | 4/1968 |
| GB | 1215609 A | 12/1970 |
| JP | 401290621 A | * 11/1989 |
| JP | 7-025764 A | 1/1995 |
| JP | 407025764 A | * 1/1995 |
| JP | 408317782 A | * 12/1996 |
| JP | 410175814 A | * 6/1998 |
| WO | 94/05649 A1 | 3/1994 |
| WO | 97/35618 A1 | 10/1997 |

OTHER PUBLICATIONS

Derwent1992-374667, Nov. 1992, Derwent, Miles Inc et al.*
Misra et al. Fungitoxic Properties of the Essential Oil of Citrus Limon(L.) Burm. Against a Few Dermatogphytes, Mycoses 31, No. 7 (1988), pp. 380-382.).*
Patent Abstract of Japan, Publication No. 7-025764, Publication Date Jan. 27, 1995.
Patent Abstract of PCT Publication No. 97/35618, Publication Date Oct. 2, 1997.
Nakatani, Nobuji, et al.; "7-Geranyloxycoumarin from Juice Oil of Hassaku (*Citrus hassaku*) and Antimicrobial Effects of Related Coumarins"; *Agricultural and Biological Chemistry*; vol. 51, No. 2, pp. 419-423; 1987.
Reverchon, Ernesto; "Supercritical fluid extraction and fractionation of essential oils and related products"; *Journal of Supercritical Fluids*; vol. 10, No. 1, pp. 1-37; Apr. 14, 1997.
Subra, Pascale, et al.; "Retention of some components in supercritical fluid chromatography and application to bergamot peel oil fractionation"; *Journal of Chromatography*; vol. 771, No. 1-2, pp. 241-250; May 30, 1997.
Matsuda, Takahiro, et al.; "Psoralen and other linear furanocoumarins as phytoalexins in *glehnia littoralis*"; *Phytochemistry*; vol. 47, No. 1, pp. 13-16; Jan. 1998.
Kwon, Yong Soo, et al.; "Antimicrobial Constituents of *Foeniculum vulgare*"; *Archives of Pharmacal Research*; vol. 25, No. 2, pp. 154-157; Apr. 2002.

* cited by examiner

*Primary Examiner*—Susan Coe
*Assistant Examiner*—Randall Winston
(74) *Attorney, Agent, or Firm*—Kubovcik & Kubovcik

(57) ABSTRACT

Provided is an antibacterial agent exhibiting an excellent antibacterial activity effect and exerting a mild influence on the environment and humans. The antibacterial agent of the present invention comprises, as an effective component, a mixture of coumarin analogues extracted from a citrus fruit pericarp, particularly a mixture of coumarin analogues obtained from citrus cold press oil.

14 Claims, No Drawings

ANTIBACTERIAL AGENT

BACKGROUND OF THE INVENTION

1. Technical Field

The present invention relates to an antibacterial agent containing coumarin analogues obtained from citrus cold press oil. This antibacterial agent exhibits excellent antibacterial ability against various bacteria, also exerts a mild influence on humans and environment and does not change flavor and taste even after it is compounded, showing that it can be used for many purposes.

2. Prior Art

Synthetic antiseptics have been developed and used in various fields. For example, synthetic antiseptics such as Trichlosane and Parabene are known in food and drink fields and cosmetic fields. These synthetic antiseptics have, to say in general, safety problems and are limited in the subjects to which these antiseptics are added and the amount to be added at present.

In the meantime, lysozyme, protamine, tea extracts, various spice extracts, various essential oils (components) and the like are known as antibacterial agents of a natural origin. However, these antibacterial agents not only are said to be by no means superior in antibacterial ability to the synthetic antiseptics but also involve such a problem that each affects the taste and flavor of the materials to which it is added.

Also, bacteria, for example, acid-thermophilic bacteria (genus *Alicyclobacillus*), which grow in favor of high temperature (40 to 70° C.) and acidic conditions (pH=2 to 6) are known. These bacteria cannot be perished in the usual bactericidal condition (86 to 96° C., 2 minutes) of soft drinks and proliferate while these drinks are stored, resulting in, for example, the occurrence of an unfavorable chemical odor, impaired taste and the occurrence of turbidity, indicating that these bacteria are a factor damaging a product value significantly. To avoid this problematic point, a method is proposed in which cane sugar fatty acid ester, which has been found to have an antibacterial effect, is added to low-acidity drinks such as coffee-flavored drinks. However, this ester has inferior dispersibility in an acidic range and is easily crystallized. From this reason, turbidity and precipitates are caused in the acidic drinks. Therefore, it is pointed out that this method has the disadvantage that the product value is impaired.

For this, there is a demand for an antibacterial agent which is of a natural origin, has superior antibacterial ability and has no influence on the taste and flavor of the product.

SUMMARY OF THE INVENTION

Accordingly, in order to solve the above problem, the present invention has the object of providing an antibacterial agent which is of a natural origin, exhibits excellent antibacterial ability, exerts a mild influence on humans and environment and has no influence on taste and flavor.

The inventors of the present invention have directed their attention to cold press oil which has been widely known and prepared from citrus fruits and have made earnest studies to prepare an antibacterial agent having more excellent antibacterial ability. As a result, the inventors have found that the solvent-eluate fraction obtained by processing a high-boiling point portion of the citrus cold press oil using a silica gel column has high antibacterial ability. Based on this finding, further studies have been made to complete the present invention.

According to the present invention, there is provided:

1) an antibacterial agent comprising a coumarin analogue obtained from a citrus fruit;

2) an antibacterial agent according to 1) wherein the coumarin analogue contains a coumarin analogue obtained from a citrus cold press oil derived from the pericarp of a citrus fruit;

3) an antibacterial agent according to 1), wherein the coumarin analogue is obtained from a high-boiling point portion of a citrus cold press oil;

4) an antibacterial agent according to 1), wherein the coumarin analogue is obtained from a fraction eluted by a solvent after a high-boiling point portion of the citrus cold press oil is carried on a support;

5) an antibacterial agent for acid-thermophilic bacteria, the antibacterial agent comprising a coumarin analogue obtained from a citrus fruit;

6) an oral care product comprising the aforementioned antibacterial agent; and 7) a food comprising the aforementioned antibacterial agent.

PREFFERED EMBODIMENT OF THE INVENTION

The present invention will be hereinafter explained in detail.

The antibacterial agent meant in the present invention is an agent comprising, as an essential component, a mixture of coumarin analogues obtained from the pericarp of citrus fruits. Although the mixture of coumarin analogues may be obtained from the above pericarp by extraction with a solvent, it may also be obtained from citrus cold press oil derived from the pericarp of citrus fruits.

The mixture of coumarin analogues meant in the present invention is obtained from the pericarp of citrus fruits and a mixture containing plural compounds selected from compounds having a coumarin skeleton and compounds having a furocoumarin skeleton. There are many known coumarin analogue mixtures. Typical examples among these mixtures include auraptene, marmin, limettin, melanzin, 5-geranoxy-7-methoxycoumarin, citropten, bergapten, bergamottin, bergaptol, epoxybergamottin, dihydroxybergamottin and 5-geranoxy-psoralen. However, these compounds are not intended to be limiting of the present invention.

The higher the content of the above coumarin analogue in the mixture of compounds obtained from the pericarp of citrus fruit, the more greatly the antibacterial ability is improved and so a higher content of the coumarin is advantageous. In the antibacterial agent of the present invention, the coumarin analogue is contained in the mixture in an amount of 40% by weight or more, more preferably 60% by weight or more and still more preferably 80% by weight or more in view of operability when it is added and compounded.

The citrus cold press oil meant in the present invention has been widely known. The citrus cold press oil is usually prepared from citrus fruits, particularly, from the pericarp thereof. The citrus cold press oil may be prepared from citrus fruits though a commercially available one may be used usually as the citrus cold press oil. As the citrus fruit, lemon, orange, lime, grapefruit, bergamot and the like are known. Among these fruits, lemon and lime are preferable in particular.

Next, explanations will be furnished as to a method for obtaining a coumarin analogue from the citrus cold press oil.

The above citrus cold press oil is separated into a high-boiling point fraction and a low-boiling point fraction by a usual method. For example, when the citrus cold press oil is fractionated by a distillation method, the citrus cold press oil is introduced into a distiller and gradually heated under reduced pressure. Then, the distillate is called a low-boiling point fraction and the residue left in the distiller is called a high-boiling point fraction. In the present invention, the high-boiling point fraction means the residue left after the citrus cold press oil is heated at 90 to 120° C. under reduced pressure (e.g., about 133 kPa). This high-boiling point fraction is a mixture consisting of nonvolatile components.

Then, this high-boiling point fraction is further fractionated. As the fractionating method, various methods are known. As a typical method, a method of fractionating using a silica gel chromatographic method will be explained.

First, the above high-boiling point fraction may be pretreated in advance. For instance, it may be thickened by heating or made to have a low viscosity by adding a solvent. In this case, it is generally preferable to add the solvent in an amount of 0.1 to 30 parts by volume and preferably 0.5 to 20 parts by volume based on one part by weight of the extract.

Then, a method may be adopted in which the high-boiling point fraction is poured into, for example, a column for chromatography which is made and adjusted in advance, then an eluent constituted of a solvent is poured into the column to flow out the fraction retained temporally in the column with the solvent and the flown-out solvent is divided into several parts by a known means. In this invention, hydrocarbons such as n-pentane, n-hexane, branched hexane, benzene and toluene may be used as a non-polar solvent. Also, as a polar solvent, esters such as methyl acetate and ethyl acetate, ethers such as ethyl ether and alcohols such as methanol, ethanol and propanol can be used. However, the solvent to be used in the present invention is not limited to these solvents.

In the case of using usual silica gel chromatography, it is preferable to flow out each fraction by using n-hexane, ethyl acetate or a mixed solvent of these solvents. When the mixed solvent is used, there is no particular limitation on the proportion of each solvent. As to the elution temperature, the elution is carried out at ambient temperature. However, no particular limitation is imposed on the temperature and the elution may be carried out either at low temperatures or at high temperatures.

In the present invention, particularly the fraction is first flown out only by hexane and then a mixed solvent of hexane and ethyl acetate is used, namely the content of hexane is decreased. Also, the fraction may be flown out only by ethyl acetate.

Next, the solvent flown out by the above method using a known means is fractionated to obtain each fraction. A fraction or a combination of plural fractions containing much coumarin analogues is processed to distill the solvents thereby obtaining a concentrate and thus an antibacterial agent can be prepared. In this case, a little solvent may be left. Furthermore, a treating step may be added in which the concentrate is treated repeatedly by refining operations such as high performance liquid chromatography. The crucial point is that the antibacterial agent is made to contain a significant coumarin analogue mixture.

The antibacterial agent thus obtained exhibits excellent antibacterial ability against various bacteria. Examples of these bacteria may include dental caries causal bacteria, periodontosis bacteria, acid-thermophilic bacteria, acne bacteria, hircismus bacteria, dandruff bacteria, skin normal bacteria, abscess bacteria and food poisoning bacteria.

As specific examples of these bacteria, the following bacteria may be mentioned.

Dental caries causal bacteria; *Streptococcus mutans, Actinomyces naeslundii, Actionmyces viscosus;*

Periodontosis bacteria; *Fusobacterium nuclestum, Prevotella intermedia, Porphyromonas gingivalis;*

Calcification bacteria; *Corynebacterium matruchotti;*

Pathogenic bacteria in a pharynx zone; *Streptococcus pyogenes, Haemophilus influenzae;*

Acid-thermophilic bacteria; *Alicyclobacillus acidocaldarius, A. acidoterrestris, A. cycloheptanicus;*

Flatsour bacteria; *Bacillus coagulans;*

Lactic acid bacteria; *Sporolactobacillus inulinus*; Butyric acid bacteria: *Clostridium pasteurianum, Clostridium butyricum;*

Eumycetes; *Byssochlamys uflva, Neosartorya fischeri;*

Acne bacteria; *Propionibacterium acnes;*

Hircismus bacteria; *Corynebacterium xerosis;*

Dandruff bacteria; *Malassezia furfur;*

Skin normal bacteria; *Staphylococcus aureus, Staphylococcus epidermides, Corynebacterium minutissimum;*

Abscess bacteria; *Bacteriodes fragilis;*

Food poisoning bacteria; *Vibrio parahaemolyticus, Campylobacter jejuni;*

Putrefying bacteria: *Bacillus subtilis*; and etc.

The antibacterial agent thus obtained may be added directly to foods and the like. Also, it is possible to subject the antibacterial agent to use by dissolving or dispersing it in a proper liquid carrier or by mixing it with or adsorbing it onto a proper powder carrier. As the case may be, emulsifiers, dispersants, suspending agents, spreaders, penetrants, wetting agents or stabilizers may be added whereby the antibacterial agent is made into preparations such as emulsions, water-dispersible powders, powders or tablets. The antibacterial agent is preferably used for foods, cosmetics and antibacterial preparations. Also, the antibacterial agent of the present invention may be used in combination with other known antibacterial agents or known compounds considered to have an antibacterial activity.

As examples of the materials to which the antibacterial agent of the present invention may be added and compounded, foods, fragrant products, fundamental cosmetics, hair cosmetics, toiletry products, bath agents, body care products, detergent/finishing agents, flavorous deodorants and drugs are given, however the present invention is not limited to these materials.

Examples of the above foods may include drinks such as a non-fruit juice drink, fruit juice-containing drink, lactic acid beverage and powdery drink, frozen sweets such as an ice cream, sherbet and ice sweet, deserts such as pudding, jelly, bavaroi and yoghurt, sweets such as a gum and candy and marine products made with boiled fish paste.

Examples of the fragrant products may include perfumes, toilet water, cologne and shower cologne.

Examples of the above fundamental cosmetics may include skin cream, cleansing cream, skin lotion, after-shave lotion, foundation, lipstick and talcum powder.

Examples of the above hair cosmetics may include shampoo agents such as a shampoo, rinse, conditioner, rinse-in-shampoo and treatment, hair dressing agents such as a pomade, hair tonic, hair liquid and hair jell, hair restorer, hair dying agent and cold wave agent.

Examples of the above toiletry products may include a toilet soap, bath soap and transparent soap.

Examples of the above bath agents may include a powdery bathing agent, solid bathing agent, solid foam bathing agent, bath oil and bubble bath.

Examples of the above detergents may include a powdery detergent for clothes, liquid detergent for clothes, softening and finishing agent, kitchen detergent, lavatory detergent, bath detergent, glass cleaner and mould-removing agent.

Examples of the above air care deodorants may include a gel-like air care deodorant, liquid air care deodorants, impregnated type air sol air care deodorant and mist type air care deodorant.

Examples of the above drugs may include a tablet, liquid drug, capsule type drug and granular drug.

Generally, the amount of the above antibacterial agent to be added to and compounded in a material is preferably 0.1 µg/ml to 50% by weight based on the material though it largely differs depending on the type of material and the type of bacterium. When the amount is less than 0.1 µg/ml, only insufficient antibacterial ability is obtained. Even if the antibacterial agent is added in an amount exceeding 50% by weight, this is economically disadvantageous though sufficient antibacterial ability is obtained.

EXAMPLES

The present invention will be explained in more detail by way of examples and comparative examples, which, however, are not intended to be limiting of the present invention.

Example 1

Preparation of an Antibacterial Agent Derived from a Lemon Pericarp 1 kg of citrus cold press oil derived from a lemon pericarp was placed in a heating container disposed in a distiller and gradually heated under reduced pressure. Volatile compounds were vaporized, liquefied in a cooler and accumulated in a receiving section. When the temperature of the citrus cold press oil in the heating container reached 120° C. under pressure, the heating was stopped. The amount of the residue (high-boiling point fraction) left in the heating container was 67 g.

A very small amount of ethyl acetate was added to 200 g of this high-boiling point fraction, which was then poured into a silica gel chromatographic column filled with 4 kg of silica gel and the high-boiling point fraction was carried on the silica gel.

Then, the fraction was eluted with 30 L of n-hexane to obtain a fraction 1. In succession, the fraction left in the column was eluted with a mixed solvent of ethyl acetate/hexane (volumetric ratio: 10:90), a mixed solvent of ethyl acetate/hexane (volumetric ratio: 20:80), a mixed solvent of ethyl acetate/hexane (volumetric ratio: 30:70), a mixed solvent of ethyl acetate/hexane (volumetric ratio: 50:50) and ethyl acetate 30 L each in volume to obtain a fraction 2, a fraction 3, a fraction 4, a fraction 5 and a fraction 6 respectively.

Each fraction was placed in an evaporator to emit the solvents thereby obtaining dry solids. The amount and coumarin analogue content of each fraction are shown in Table 1. Here, the content of the coumarin analogues is measured using a method in which 4 mg of the dry solid is dissolved in 50 ml of n-hexane or ethyl acetate and the solution was irradiated with ultraviolet light (wavelength: 311 nm) to measure the value of light absorption, from which the content is found.

TABLE 1

Yield and coumarin analogue content of each fraction

| Fraction # | Lemon | Lime |
|---|---|---|
| 1 | 30 (0)* | 23 (1) |
| 2 | 34 (18) | 22 (31) |
| 3 | 20 (87) | 15 (100) |
| 4 | 6 (99) | 17 (100) |
| 5 | 5 (99) | 19 (91) |
| 6 | 5 (63) | 4 (89) |

(weight %)
*X (Y)
X = Yield based on the nonvolatile fraction
(Y) = Content of coumarin analogues in the fraction The mixture of the dry solids obtained from each of the fractions 3, 4, 5 and 6 are called a coumarin analogue high concentration fraction and the mixture of the dry solids obtained from the fractions 1 and 2 are called a coumarin analogue low concentration fraction. Also, the mixtures of the dry solids obtained from the fractions 3 and 4 are called a concentrated fraction of the coumarin analogue high concentration fraction.

The above coumarin analogue high concentration fraction was dissolved in ethanol so as to adjust the solution to a concentration of 20% by weight to obtain a solution of the coumarin analogue high concentration fraction (CCF solution). Also, the concentrated fraction of the above coumarin analogue high concentration fraction was dissolved in ethanol so as to adjust the solution to a concentration of 20% by weight to obtain a solution of the concentrated fraction of the coumarin analogue high concentration fraction (CCMF solution)

Example 2

Preparation of an Antibacterial Agent Derived from a Lime Pericarp

The same procedures as in Example 1 were carried out except that citrus cold press oil derived from a lime pericarp was used in place of the citrus cold press oil derived from a lemon pericarp, to obtain a coumarin analogue high concentration fraction, a concentrated fraction of the coumarin analogue high concentration fraction and a coumarin analogue low concentration fraction.

Further, the same operation as in Example 1 was carried out to obtain a solution of the coumarin analogue high concentration fraction (CCF solution) and a solution of the concentrated fraction of the coumarin analogue high concentration fraction (CCMF solution).

Test Example 1

Test for Antibacterial Ability (Measurement of Minimum Inhibitory Concentration (MIC) Using an Agar Medium Dilution Method)

The samples shown below were dissolved in ethanol to prepare a serial twofold dilution stage and 100 µL of each was added to 10 mL of a sterilized agar medium (Trypticase Soy Agar (BBL)), which was then stirred sufficiently, then transferred to a 9-cm-diameter Petri dish and solidified at ambient temperature. 5 µL of a diluted test bacteria (shown below) solution was implanted in the Petri dish and cultured at 37° C. for 72 hours. After the culturing was finished, the growth state of the medium in this Petri dish was compared with that in a Petri dish (blank) containing no sample and the concentration of the sample in which the growth of bacteria was not seen was defined as MIC. The results obtained are shown in Table 2.

Sample

S-1: Coumarin analogue high concentration fraction derived from lemon cold press oil S-2: Concentrated fraction of a coumarin analogue high concentration fraction derived from lemon cold press oil S-3: Coumarin analogue high concentration fraction derived from lime cold press oil S-4: Concentrated fraction of a coumarin analogue high concentration fraction derived from lime cold press oil Control Plot C-1: Trichlosane
C-2: Butylparabene
C-3: Coumarine analogue low concentration fraction derived from lemon cold press oil
C-4: Coumarine analogue low concentration fraction derived from lime cold press oil Test Bacteria (Dental Caries Causal Bacteria)
(a) *Streptococcus mutans* JCM 5175
(b) *Actinomyces naeslundii* JCM 8350
(c) *Actionmyces viscosus* JCM 8352

(Periodontosis Bacteria)
(d) *Fusobacterium nuclestum* JCM 6328
(e) *Prevotella intermedia* JCM 6322
(f) *Porphyromonas gingivalis* JCM 8525 centration of the sample in which the growth of bacteria was not seen was defined as minimum inhibitory concentration (MIC).

The results obtained are shown in Table 3.

Test Bacteria

| (Food poisoning bacteria) | | | |
|---|---|---|---|
| *Staphylococcus aureus* | 209P | IAM | 12082 |
| *Staphylococcus aureus* | ATCC | 6538 | |
| (Putrefying bacteria) | | | |
| *Bacillus subtilis* | PCI | 219 | IFO | 3134 |

Qualification Method 2:

Measurements of MIC and Minimum Bactericidal Concentration (MBC) by using a Liquid Medium Dilution Method The serial twofold dilution solution of the sample is prepared in the same manner as in the agar medium dilution method. 30 µL of the sample solution having each concentration is added to 3 mL of a liquid medium (NYG medium), to which is further added 60 µL of a test bacteria solution and the medium is cultured at 30° C. for 48 hours.

A change of the turbidity of the medium is measured using a wavelength of 660 nm to find MIC. The media 60 µL each are taken out from a test tube in which no growth of the bacteria is found and implanted in 3 mL of a new medium

TABLE 2

| | Qualification of activity (MIC: ppm) | | | | | | | |
|---|---|---|---|---|---|---|---|---|
| Bacterium | C-1 | C-2 | C-3 | C-4 | S-1 | S-2 | S-3 | S-4 |
| (a) *Streptococcus mutans* | 6.3 | 200 | >1000 | >1000 | 100 | 100 | 100 | 100 |
| (b) *Actinomyces naeslundii* | 3.1 | 100 | >1000 | >1000 | 12.5 | 12.5 | 12.5 | 12.5 |
| (c) *Actionmyces viscosus* | 3.1 | 100 | >1000 | >1000 | 12.5 | 12.5 | 6.3 | 3.1 |
| (d) *Fusobacterium nuclestum* | 3.1 | 100 | >1000 | >1000 | 12.5 | 6.3 | 6.3 | 3.1 |
| (f) *Porphyromonas gingivalis* | 3.1 | 50 | >1000 | >1000 | 6.3 | 6.3 | 3.1 | 1.6 |
| (e) *Prevotella intermedia* | 3.1 | 100 | >1000 | >1000 | 12.5 | 25.0 | 3.1 | 12.5 |

The antibacterial agent of the present invention was observed to have a strong antibacterial activity equal to that of trichlosane.

Test Example 2

Test for Antibacterial Ability (Measurement of Minimum Inhibitory Concentration (MIC) Using an Agar Medium Dilution Method)

Qualification Test Method 1:

Measurement of Minimum Inhibitory Concentration (MIC) Using an Agar Medium Dilution Method The samples shown below were dissolved in ethanol to prepare a serial twofold dilution stage and 100 µL of each was added to 10 mL of a sterilized agar medium (Mueller Hinton medium (Difco)), which was then stirred sufficiently, then transferred to a 9-cm-diameter Petri dish and solidified at ambient temperature. 5 µL of a diluted test bacteria solution was implanted in the Petri dish and cultured at 37° C. for 72 hours. After the culturing was finished, the growth state of the medium in this Petri dish was compared with that in a Petri dish (blank) containing no sample and the conand cultured for 48 hours. The minimum concentration at which no growth of the bacteria was observed is defined MBC.

The results are shown in Table 4.

Sample

S-1: Coumarin analogue high concentration fraction derived from lemon cold press oil S-2: Concentrated fraction of a coumarin analogue high concentration fraction derived from lemon cold press oil S-3: Coumarin analogue high concentration fraction derived from lime cold press oil S-4: Concentrated fraction of a coumarin analogue high concentration fraction derived from lime cold press oil Control Plot C-1: Trichlosane
C-2: Butylparabene
C-3: Coumarine analogue low concentration fraction derived from lemon cold press oil
C-4: Coumarine analogue low concentration fraction derived from lime cold press oil Test Bacteria

| (Food poisoning bacteria) | | | |
|---|---|---|---|
| *Staphylococcus aureus* | 209P | IAM | 12082 |
| *Staphylococcus aureus* | ATCC | 6538 | |
| (Putrefying bacteria) | | | |
| *Bacillus subtilis* | PCI | 219 | IFO | 3134 |

TABLE 3

Qualification of activity using a qualification test method 1 (MIC: ppm):

| Bacterium | C-2 | C-3 | C-4 | S-2 | S-4 |
|---|---|---|---|---|---|
| *Bacillus subtilis* PCI 219 | 200 | >1000 | >1000 | 25 | 6.3 |
| *Staphylococcus aureus* 209P | 100 | >1000 | >1000 | 12.5 | 6.3 |
| *Staphylococcus aureus* ATCC | 200 | >1000 | >1000 | 25 | 6.3 |

The samples S-2 and S-4 used in an amount in the order of ppm were observed to have more effective antibacterial activity against the above test bacteria.

TABLE 4

Qualification of activity using a qualification test method 2 (MIC, MBC: ppm)

| BACTERIUM | C-1 | S-1 | S-3 |
|---|---|---|---|
| MIC | | | |
| *Staphylococcus aureus* IAM12082 | 0.244 | 3.91 | 1.95 |
| *Staphylococcus aureus* ATCC 6538 | 0.977 | 3.91 | 3.91 |
| MBC | | | |
| *Staphylococcus aureus* IAM12082 | 0.977 | 62.5 | 15.6 |
| *Staphylococcus aureus* ATCC6538 | 1.95 | 500.0 | 250.0 |

From the results of the measurement of MBC, trichlosane has strong bactericidal activity, whereas the samples S-1 and S-3 are bacteriostatic and therefore the antibacterial effect of these samples may be concluded to be due to the bacteriostatic action. Therefore, the samples S-1 and S-3 may be concluded to exert a mild influence on humans and the environment.

Test Example 3

Test for Antibacterial Ability

Test Method 1) 0.5 mL of a standard strain solution stored in sterilized-purified water is diluted with 5 mL of sterilized phosphoric acid buffer physiological salt solution. After the diluted strain solution is heated at 80° C. for 10 minutes, it is added to each AAM liquid medium having a volume of 5 mL in an amount of 100 μL (the number of spores in 100 μL=about 1,000,000).

2) The sample is added to the AAM liquid medium implanted with the standard bacteria such that it is contained in each concentration.

3) The AAM liquid medium is cultured at 50° C. for 10 days.

4) Whether the bacteria which go into operation are present or not is observed using a microscope (the bacteria is globular when they form a spore and are in a dormant stage but the bacteria which go into operation become bacilli, so that both can be easily discriminated from each other by using a microscope).

The results obtained by the observation using a microscope are shown in Table 5. The case where any bacterium which germinates are not present at all is evaluated as (−) and the case where the presence of a bacterium which germinates is confirmed is evaluated as (+)

AAM (*Alicyclobacillus Acidoterrestris* Medium) liquid medium:

| (Solution A) | |
|---|---|
| $CaCl_2.2H_2O$ | 0.25 g |
| $MgSO_4.7H_2O$ | 0.50 g |
| $(NH_4)_2SO_4$ | 0.20 g |
| Yeast extract | 2.00 g |
| Glucose | 5.00 g |
| $KH_2PO_4$ | 3.00 g |
| Water | 1000.00 mL |
| Adjusted to pH 4.0 using 1 M HCl solution | |
| (Solution B) | |
| Trace element solution SL-6 | 1.00 mL |
| SL-6 | |
| $ZnSO_4.7H_2O$ | 0.10 g |
| $MnCl_2.4H_2O$ | 0.03 g |
| $H_3BO_3$ | 0.30 g |
| $CoCl_2.6H_2O$ | 0.20 g |
| $CuCl_2.2H_2O$ | 0.01 g |
| $NiCl_2.6H_2O$ | 0.02 g |
| $Na_2MoO_4.2H_2O$ | 0.03 g |
| Water | 1000.00 mL |

The solution A and the solution B are mixed to obtain an AAM liquid medium.

Sample

S-1: Coumarin analogue high concentration fraction derived from lemon cold press oil S-2: Concentrated fraction of a coumarin analogue high concentration fraction derived from lemon cold press oil S-3: Coumarin analogue high concentration fraction derived from lime cold press oil S-4: Concentrated fraction of a coumarin analogue high concentration fraction derived from lime cold press oil Test Bacteria (Genus *Alicyclobacillus*)

*Alicyclobacillus acidocaldarius*

*A. acidoterrestris*

*A. cycloheptanicus*

(Flatsour Bacteria)

*Bacillus coagulans*

TABLE 5

| | Amount added (ppm) | Alicyclobacillus acidocaldarius | A. acido terrestris | A. cyclo heptanicus | Bacillus coagulans |
|---|---|---|---|---|---|
| S-1 | 5 | ± | ± | ± | – |
| | 50 | – | – | – | – |
| S-2 | 0.5 | ± | ± | ± | ± |
| | 5 | – | – | – | – |
| | 50 | – | – | – | – |
| S-3 | 5 | ± | ± | ± | – |
| | 50 | – | – | – | – |
| S-4 | 0.5 | ± | ± | ± | ± |
| | 5 | – | – | – | – |
| | 50 | – | – | – | – |

Explanations of the Symbols in the Table

"–" indicates the case where no bacterium which germinates are present.

"±" indicates the case where bacteria which germinate are observed though the number of such bacteria is very small (several bacteria).

Test Example 4

Test for Antibacterial Ability (Measurement of Minimum Inhibitory Concentration (MIC) Using an Agar Medium Dilution Method)

The samples were dissolved in ethanol to prepare a serial twofold dilution stage and 100 μL of each was added to 10 mL of a sterilized agar medium, which was then stirred sufficiently, then transferred to a 9-cm-diameter Petri dish and solidified at ambient temperature. 5 μL of a diluted test bacteria solution was implanted in the Petri dish and cultured at 37° C. for 72 hours. After the culturing was finished, the growth state of the medium in this Petri dish was compared with that in a Petri dish (blank) containing no sample and the concentration of the sample in which the growth of bacteria was not seen was defined as minimum inhibitory concentration (MIC).

The results obtained are shown in Table 6.

Sterilized Agar Medium:

| | | | |
|---|---|---|---|
| (a) *Propionibacterium acnes* | JCM | 6473 | |
| (b) *Propionibacterium acnes* | ATCC | 6919 | |
| (c) *Bacteriodes fragilis* | GAI | 5560 | |
| Trypticase Soy Agar (BBL) in these cases | | | |
| (d) *Corynebacterium xerosis* | JCM | 1324 | |
| (e) *Malassezia furfur* | IFO | 0656 | |
| (f) *Staphylococcus epidermides* | JCM | 2414 | |
| (g) *Corynebacterium minutissimum* | IFO | 15361 | |

Mueller Hinton Medium (Difco) in these Cases

Sample

S-1: Coumarin analogue high concentration fraction derived from lemon cold press oil S-2: Concentrated fraction of a coumarin analogue high concentration fraction derived from lemon cold press oil S-3: Coumarin analogue high concentration fraction derived from lime cold press oil S-4: Concentrated fraction of a coumarin analogue high concentration fraction derived from lime cold press oil Control Plot C-2: Butylparabene C-3: Coumarine analogue low concentration fraction derived from lemon cold press oil C-4: Coumarine analogue low concentration fraction derived from lime cold press oil Test Bacteria

| | | |
|---|---|---|
| (Acne bacteria) | | |
| *Propionibacterium acnes* | JCM | 6473 |
| *Propionibacterium acnes* | ATCC | 6919 |
| (Hircismus bacteria) | | |
| *Corynebacterium xerosis* | JCM | 1324 |
| (Dandruff bacteria) | | |
| *Malassezia furfur* | IFO | 0656 |
| (Skin normal bacteria) | | |
| *Staphylococcus epidermides* | JCM | 2414 |
| *Corynebacterium minutissimum* | IFO | 15361 |
| (Abscess bacteria) | | |
| *Bacteriodes fragilis* | GAI | 5560 |

TABLE 6

Minimum inhibitory concentration (MIC): ppm

| Bacterium | C-2 | C-3 | C-4 | S-1 | S-2 | S-3 | S-4 |
|---|---|---|---|---|---|---|---|
| (f) *Staphylococcus epidermides* | 200 | — | — | 50 | 25 | 12.5 | 12.5 |
| (g) *Corynebacterium minutissimum* | 200 | — | — | 25 | 12.5 | 6.3 | 3.1 |
| (d) *Corynebacterium xerosis* | 50 | — | — | 25 | 12.5 | 12.5 | 6.3 |
| (e) *Malassezia furfur* | 100 | — | — | 12.5 | 12.5 | 6.3 | 6.3 |
| *Bacillus subtilis* PCI 219 | 200 | — | — | 25 | 25 | 12.5 | 6.3 |
| (a) *Propionibacterium acnes* JCM 6473 | 100 | >1000 | >1000 | 12.5 | 12.5 | 6.3 | 6.3 |

TABLE 6-continued

| | Minimum inhibitory concentration (MIC): ppm | | | | | | |
|---|---|---|---|---|---|---|---|
| Bacterium | C-2 | C-3 | C-4 | S-1 | S-2 | S-3 | S-4 |
| (b) *Propionibacterium acnes* ATCC 6919 | 100 | >1000 | >1000 | 12.5 | 12.5 | 6.3 | 3.1 |
| (c) *Bacteriodes fragilis* | 50 | — | — | 25 | 25 | 3.1 | 3.1 |

In the table, "−" indicates that no experiment was made.

(Example 3) Toothpaste

| | |
|---|---|
| Dicalcium phosphate | 10.0% by weight |
| Sodium laurylsulfate | 2.0 |
| Sodium carboxymethyl cellulose | 0.5 |
| Sodium saccharide | 0.02 |
| Peppermint flavor | 1.0 |
| CCF solution | 5.0 |
| Glycerol | Proper amount |
| | 100.0% by weight |

(Example 4) Mouth detergent

| | |
|---|---|
| Ethyl alcohol | 10.0% by weight |
| Polyoxyethylene hydrogenated castor oil | 2.0 |
| Peppermint flavor | 0.5 |
| Sodium saccharide | 0.02 |
| Glycerol | 10.0 |
| FD & Color | |
| CCF solution | 0.25 |
| Purified water | Proper amount |
| | 100.0% by weight |

(Example 5) Candy

| | |
|---|---|
| Sugar powder | 50.0% by weight |
| Starch syrup | 33.0 |
| Citric acid | 1.0 |
| CCF solution | 0.25 |
| Purified water | Proper amount |
| | 100.0% by weight |

(Example 6) Chewing gum

| | |
|---|---|
| Gum base | 21.0% by weight |
| Sugar powder | 63.9 |
| Corn starch | 12.5 |
| Lemon type flavor | 1.0 |
| Acidifying agent | 0.6 |
| CCF solution | 0.25 |
| | 100.0% by weight |

(Example 7) Lozenge

| | |
|---|---|
| Starch | 98.45% by weight |
| Peppermint type powder flavor | 0.8 |
| Sucrose fatty acid ester | 0.5 |
| CCMF solution | 0.25 |
| | 100.0% by weight |

(Example 8) De-bacterial agent

| | |
|---|---|
| Ethanol | 20.0% by weight |
| CCMF solution | 5.0 |
| Purified water | Proper amount |
| | 100.0% by weight |

(Example 9) Fruit juice drink

| | |
|---|---|
| Orangeade (Brix: 10.8, acidity: 0.38) | 107.0 g |
| Fructose, glucose, liquid sugar | |
| Citric acid | 1.0 |
| Sodium citrate | 0.3 |
| Orange concentrated fruit juice | 51.8 |
| Water-soluble orange flavor | 1.0 |
| CCF solution | 0.1 |
| Water | Proper amount |
| | 1000 g |

(Example 10) Sport drink

| | |
|---|---|
| Sugar | 31.0 g |
| Glucose | 15.7 |
| Citric acid | 1.0 |
| Calcium lactate | 0.679 |
| Sodium citrate | 0.3 |
| Sodium chloride | 0.28 |
| Potassium chloride | 0.22 |
| Vitamin C | 0.864 |
| Sodium L-glutamate | 0.03 |
| Niacin | 0.013 |
| Calcium pantothenate | 0.007 |
| Vitamin B6 | 0.0022 |
| Vitamin B12 | 0.000006 |
| Lemon flavor | 1.0 |
| CCMF solution | 0.1 |
| Purified water | Proper amount |
| | 1000 g |

(Example 11) Coffee-flavored drink

| | |
|---|---|
| Regular coffee | 50.0 g |
| Granulated sugar | 50.0 |
| Milk | 150.0 |
| Emulsifier (fatty acid ester) | 0.5 |
| Coffee flavor | 1.0 |
| Milk flavor | 0.8 |
| CCMF solution | 0.1 |
| Purified water | Proper amount |
| | 1000.0 g |

(Example 12) Carbonated drink

| | |
|---|---|
| Fructose, glucose, liquid sugar | 127.0 g |
| Citric acid | 1.24 |
| Purified water | 200.0 |
| Lemon flavor | 0.12 |
| CCMF solution | 0.05 |
| Carbonated water | Proper amount |
| | 1000.0 g |

(Example 13) Fruit juice jelly

| | |
|---|---|
| Apple juice | 6.0 g |
| Starch syrup | 3.5 |
| Granulated sugar | 13.0 |
| Malic acid | 0.21 |
| Gelling agent | 0.9 |
| Sodium citrate | 0.05 |
| Caramel dye | 0.08 |
| Apple flavor | 0.2 |
| CCMF solution | 0.01 |
| Purified water | Proper amount |
| | 100.0 g |
| Sterilized at 80° C. for 20 minutes | |

(Example 14) Lemon tea

| | |
|---|---|
| Black tea leaves (Bx. 1.0) | 200.0 g |
| Granulated sugar | 60.0 |
| Lemon concentrated fruit juice | 1.56 |
| Vitamin C | 0.1 |
| CCMF solution | 0.05 |
| Purified water | Proper amount |
| | 1000.0 g |

-continued

Sterilized at 80° C. for 10 minutes
(Example 15) Powder detergent

| | |
|---|---|
| C-12–C-18 Palay sodium sulfate | 15.0 g |
| Sodium carbonate | 15.0 |
| Sodium methasilicate | 13.0 |
| Sodium citrate | 15.0 |
| Carboxymethyl cellulose | 2.0 |
| Sodium sulfate | 38.0 |
| Musk tree type flavor | 1.0 |
| CCF solution | 1.0 |
| | 100.0 g |

(Example 16) Shampoo

| | |
|---|---|
| Sodium Laureth Sulfate | 40.0 g |
| Sodium Cocoamphoacetate | 10.0 |
| Cocamide DEA | 2.0 |
| Butylene Glycol | 2.0 |
| Citric Acid | 0.35 |
| Sodium Chloride | 0.1 |
| Paraben | 0.3 |
| Tetrasodium EDTA | 0.1 |
| Flavor | 0.5 |
| CCF solution | 1.0 |
| Purified water | Proper amount |
| | 100.0 g |

(Example 17) Emollient cream

| | |
|---|---|
| Cetyl alcohol | 5.0 g |
| Stearic acid | 3.0 |
| Vaseline | 5.0 |
| Squalane | 10.0 |
| Glycerol tri2-ethylhexanate | 7.0 |
| Dipropylene glycol | 5.0 |
| Glycerol | 5.0 |
| Propylene glycol monostearate | 3.0 |
| POE (20) cetyl alcohol ether | 3.0 |
| Triethanolamine | 1.0 |
| Parabene | 0.3 |
| Perfume | 1.0 |
| CCF solution | 1.0 |
| Purified water | Proper amount |
| | 100.0 g |

(Example 18) Antiperspirant

| | |
|---|---|
| PEG-7 glyceryl cocoate | 2.0 g |
| Hydrogenated oil | 5.0 |
| Myristyl Myristate | 15.0 |
| Cyclometicone | 35.0 |
| Stearyl alcohol | 20.0 |
| Stearyl Isononenoate | 3.0 |
| Al-chlorohydrate | 20.0 |
| Perfume | 0.5 |
| CCF solution | 1.0 |
| | 100.0 g |

The antibacterial agent obtained in the present invention and comprising a mixture of coumarin analogues derived from citrus fruit has high antibacterial ability. Specifically, the antibacterial agent of the present invention exhibits the same high antibacterial ability as a synthetic bactericidal agent against various bacteria such as bacteria relative to oral care, e.g., dental caries bacteria and periodontosis bacteria, acid-thermophilic bacteria posing a problem in food industries, food poisoning bacteria and putrefying bacteria and acne bacteria, dandruff bacteria and skin normal bacteria posing a problem in cosmetic fields. An influence on the flavor of foods of the antibacterial agent of the present invention is decreased and exerts a mild influence on humans and environment. In addition, the antibacterial agent of the present invention is highly stable and therefore remarkably useful. This antibacterial agent can be widely used and, in particular, can be applied to cosmetics and foods and drinks.

Among the above bacteria, putrefying bacteria cause, for instance, the putrefaction and deterioration of foods and therefore greatly damage the commercial value of the foods. Food poisoning bacteria cause the putrefaction and deterioration of foods and at the same time, generate poisonous substances, which bring about seriously bad influence on those who eat such foods.

Therefore, by adding the antibacterial agent of the present invention to foods, the effect of improving the stability of foods stored for a long time and the effect of preventing food poisoning are attained.

Also, acid-thermophilic bacteria (genus Alicyclobacillus) grow in favor of high temperature (40 to 70° C.) and acidic (pH 2 to 6) conditions and acid-thermophilic mold (genus *Byssochlamys*) also grow in high temperature and acidic conditions as mentioned above. These bacteria have heat resistance and cannot be killed, for instance, under the usual bactericidal conditions (96 to 86° C., 2 minutes) of soft drinks. Accordingly, the above acid-thermophilic bacteria can proliferate in highly acidic foods (e.g., canned drinks and acidic drinks containing fruits or fruit juice) having a pH less than 3.7, causing, for example, the occurrence of an unfavorable chemical odor, impaired taste and the occurrence of turbidity, indicating that these bacteria are a factor significantly damaging a product value.

The use of the antibacterial agent of the present invention prevents the proliferation of thermostable acid-fast bacteria, thereby solving the aforementioned problem and can prevent the denaturation and putrefaction of foods and drinks without causing turbidity and precipitation.

Moreover, since the antibacterial agent has the ability to inhibit the growth of dental caries bacteria, it can prevent the promotion of tooth decay and also the formation of dental plaque. Since the antibacterial agent of the present invention also has the ability to inhibit the growth of periodontosis bacteria, it not only prevents periodontosis but also inhibits the growth of bacteria which are a halitosis generating source and therefore an indirect deodorant effect can be expected. Also, because the growth of pathogenic bacteria in a pharynx zone and fungi is suppressed, it can be expected to help prevent catching colds.

Moreover, the antibacterial agent of the present invention has the effect of suppressing the growth of hircismus bacteria, dandruff bacteria and abscess bacteria. Therefore, the effect of preventing body odor, anti-dandruff effect and anti-pimple effect are expected by including the antibacterial agent of the present invention in various cosmetics.

Also, an unpleasant odor of washing which is generated when the washing is half-dried as experienced sometimes in the rainy season and the like is regarded to be largely caused by the growth of bacteria. This unpleasant odor is more reduced by including the present inventive product in a washing detergent.

The present inventive product can be used together with other antibacterial agents and materials having antibacterial activities. Moreover, the present invention ensures that the high-boiling portion of cold press oil, which portion is sometimes scrapped, can be utilized effectively.

What is claimed is:

1. An antibacterial agent comprising a mixture of non-volatile compounds obtained by fractionation of the high-boiling point portion of a citrus cold press oil that has been separated into a low-boiling point portion and a high-boiling point portion, said mixture of nonvolatile compounds containing 40% by weight or more of coumarin analogues.

2. An antibacterial agent according to claim 1, wherein the coumarin analogues are obtained from a fraction eluted by a solvent after the high-boiling point portion of the citrus cold press oil is carried on a support.

3. An antibacterial agent for thermostable acid-fast bacteria, the antibacterial agent comprising a mixture of nonvolatile compounds obtained by fractionation of the high-boiling point portion of a citrus cold press oil that has been separated into a low-boiling point portion and a high-boiling point portion, said mixture of nonvolatile compounds containing 40% by weight or more of coumarin analogues.

4. An oral care product comprising an antibacterial effective amount of the antibacterial agent as claimed in claim 1.

5. An oral care product comprising an antibacterial effective amount of the antibacterial agent as claimed in claim 2.

6. A food comprising an antibacterial effective amount of the antibacterial agent as claimed in claim 1.

7. A food comprising an antibacterial effective amount of the antibacterial agent as claimed in claim 2.

8. An antibacterial agent according to claim 1, wherein the coumarin analogues are a mixture of auraptene, marmin, limettin, melanzin, 5geranoxy-7-methoxycoumarin, citropten, bergapten, bergamottin, bergaptol, epoxybergamottin, dihydroxybergamottin and 5-geranoxy-psoralen.

9. An antibacterial agent according to claim 2, wherein the coumarin analogues are a mixture of auraptene, marmin, limettin, melanzin, 5-geranoxy-7-methoxycoumarin, citropten, bergapten, bergamottin, bergaptol, epoxybergamottin, dihydroxybergamottin and 5-geranoxy-psoralen.

10. An antibacterial agent for thermostable acid-fast bacteria according to claim 3, wherein the coumarin analogues are a mixture of auraptene, marmin, limettin, melanzin, 5-geranoxy-7-methoxycoumarin, citropten, bergapten, bergamottin, bergaptol, epoxybergamottin, dihydroxybergamottin and 5-geranoxy-psoralen.

11. An oral care product according to claim 4, wherein the coumarin analogues are a mixture of auraptene, marmin, limettin, melanzin, 5-geranoxy-7-methoxycoumarin, citropten, bergapten, bergamottin, bergaptol, epoxybergamottin, dihydroxybergamottin and 5-geranoxy-psoralen.

12. An oral care product according to claim 5, wherein the coumarin analogues are a mixture of auraptene, marmin, limettin, melanzin, 5-geranoxy-7-methoxycoumarin, citropten, bergapten, bergamottin, bergaptol, epoxybergamottin, dihydroxybergamottin and 5-geranoxy-psoralen.

13. A food according to claim 4, wherein the coumarin analogues are a mixture of auraptene, marmin, limettin, melanzin, 5-geranoxy-7-methoxycoumarin, citropten, bergapten, bergamottin, bergaptol, epoxybergamottin, dihydroxybergamottin and 5-geranoxy-psoralen.

14. A food according to claim 7, wherein the coumarin analogues ares a mixture of auraptene, marmin, limettin, melanzin, 5-geranoxy-7-methoxycoumarin, citropten, bergapten, bergamottin, bergaptol, epoxybergamottin, dihydroxybergamottin and 5-geranoxy-psoralen.

\* \* \* \* \*